(12) United States Patent
Vedrine et al.

(10) Patent No.: US 8,469,923 B2
(45) Date of Patent: Jun. 25, 2013

(54) CARTRIDGE FOR POWDER AND LIQUID DRUG

(75) Inventors: Lionel Vedrine, Ridgewood, NJ (US); Roger W. Groskopf, Saddle Brook, NJ (US); Matthew Sweeney, Montclair, NJ (US); Dnyanesh A. Talpade, Monmouth Junction, NJ (US); Min Wei, Morris Plains, NJ (US); Ruane Jeter, Wyckoff, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 280 days.

(21) Appl. No.: 12/679,508

(22) PCT Filed: Sep. 29, 2008
(Under 37 CFR 1.47)

(86) PCT No.: PCT/US2008/078113
§ 371 (c)(1),
(2), (4) Date: Oct. 12, 2010

(87) PCT Pub. No.: WO2009/043000
PCT Pub. Date: Apr. 2, 2009

(65) Prior Publication Data
US 2012/0209171 A1   Aug. 16, 2012

Related U.S. Application Data

(60) Provisional application No. 60/995,547, filed on Sep. 27, 2007, provisional application No. 61/011,255, filed on Jan. 16, 2008.

(51) Int. Cl.
*A61M 37/00* (2006.01)
(52) U.S. Cl.
USPC ............................. 604/87; 604/89; 604/414

(58) Field of Classification Search
USPC .................... 604/85, 87, 89, 90, 92, 191, 414
See application file for complete search history.

(56) References Cited

U.S. PATENT DOCUMENTS 4,059,109 A    11/1977  Tischlinger
4,226,236 A *  10/1980  Genese ........................... 604/89

(Continued)

FOREIGN PATENT DOCUMENTS

EP    0815886 A2    1/1998
JP    07148261      6/1995

(Continued)

*Primary Examiner* — Theodore Stigell
*Assistant Examiner* — Gerald Landry, II
(74) *Attorney, Agent, or Firm* — Hoffmann & Baron, LLP

(57) ABSTRACT

A cartridge or injector for holding and mixing a medical product is provided herein including a tubular body having a cylindrical wall having first and second opposing ends. The wall includes inner and outer surfaces with the inner surface having a generally constant cross-section along at least a drug mixing area. A first stopper is slidably disposed within the wall between the first and second ends, the first stopper defining a liquid-tight seal with the inner surface. A second stopper is slidably disposed within the wall between the first stopper and the first end, the second stopper defining a liquid-tight seal with the inner surface. A flexible insert is disposed at or in proximity to the second end, the insert forming a liquid-tight seal with the wall, the insert being pierceable by a medical needle or other piercing instrument. A rigid retainer is fixed to the wall having an opening therein for providing access to the insert for piercing by a medical needle. The insert extends into the retainer and forms a liquid-tight seal across the opening. Advantageously, with the subject invention, a reconstitution assembly may be provided which has a sufficiently large distal opening during assembly which allows a dry component to be introduced into the device in a dry state.

17 Claims, 13 Drawing Sheets

U.S. PATENT DOCUMENTS

| | | | |
|---|---|---|---|
| 4,613,326 A | | 9/1986 | Szwarc |
| 4,792,329 A | * | 12/1988 | Schreuder .................. 604/90 |
| 5,139,490 A | * | 8/1992 | Vetter et al. ............... 604/201 |
| 5,554,134 A | | 9/1996 | Bonnichsen |
| 5,817,056 A | * | 10/1998 | Tanaka et al. ............... 604/89 |
| 5,865,798 A | * | 2/1999 | Grimard et al. ............. 604/89 |
| 5,865,799 A | * | 2/1999 | Tanaka et al. ............... 604/89 |
| 5,935,101 A | * | 8/1999 | Kato et al. .................. 604/82 |
| 6,142,977 A | * | 11/2000 | Kolberg et al. ............. 604/218 |
| 6,319,225 B1 | * | 11/2001 | Sugita et al. ............... 604/89 |
| 6,740,060 B2 | * | 5/2004 | Tanaka et al. ............... 604/90 |
| 2005/0028489 A1 | * | 2/2005 | Forsberg et al. ............. 53/440 |
| 2006/0151629 A1 | * | 7/2006 | Vedrine et al. ............. 239/329 |
| 2006/0178638 A1 | | 8/2006 | Reynolds |
| 2007/0185440 A1 | * | 8/2007 | Matsumto et al. ........... 604/85 |

FOREIGN PATENT DOCUMENTS

| | | | |
|---|---|---|---|
| WO | WO 93/20869 A1 | * | 4/1993 |
| WO | 93/20867 A1 | | 10/1993 |
| WO | 93/20869 A1 | | 10/1993 |
| WO | 9320868 | | 10/1993 |
| WO | 99/15215 A1 | | 4/1999 |

* cited by examiner

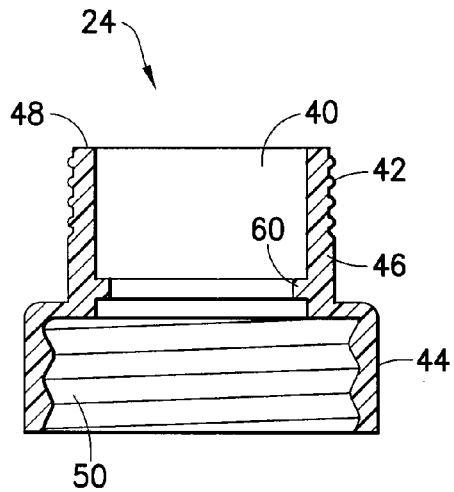
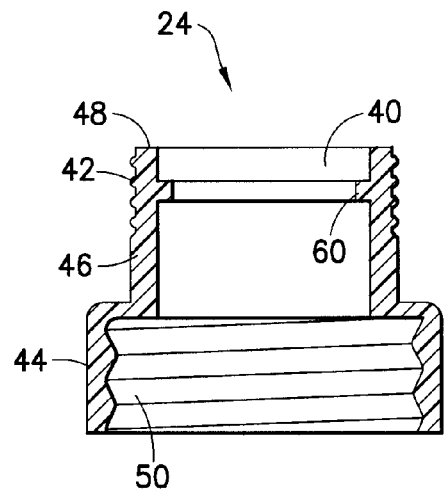
FIG.5　　　　　FIG.6
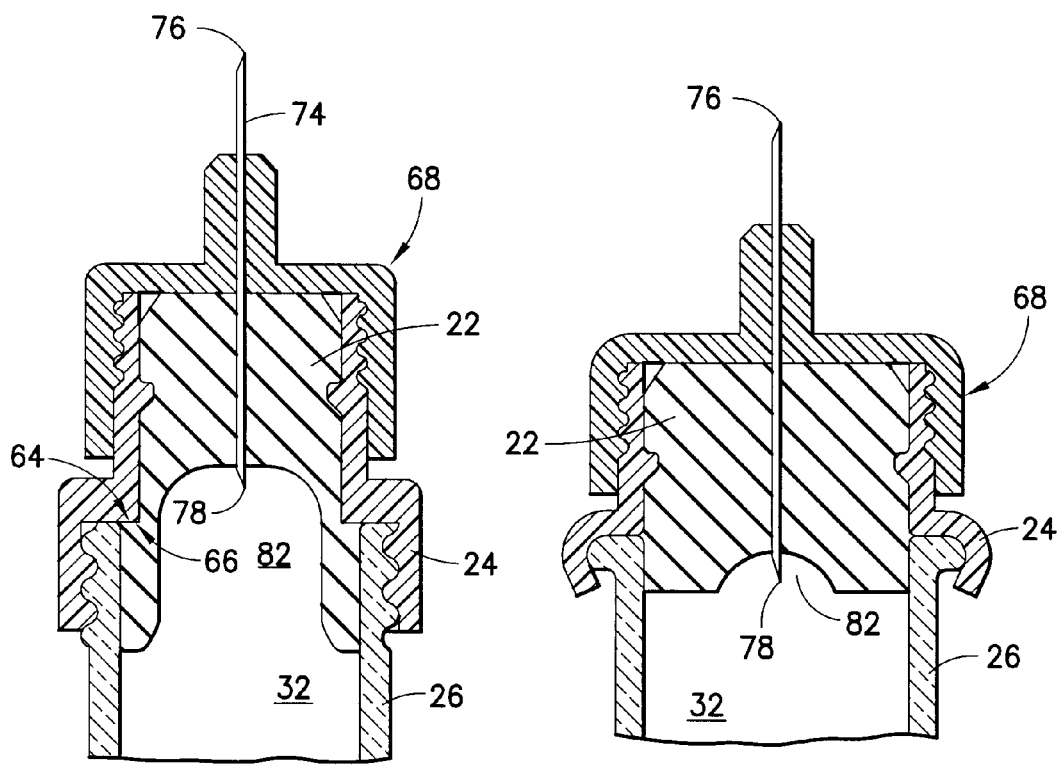
FIG.7　　　　　FIG.8

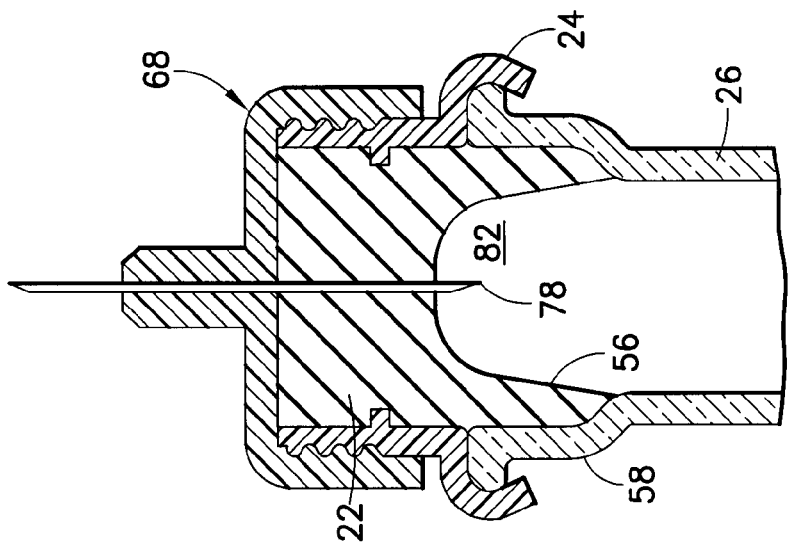
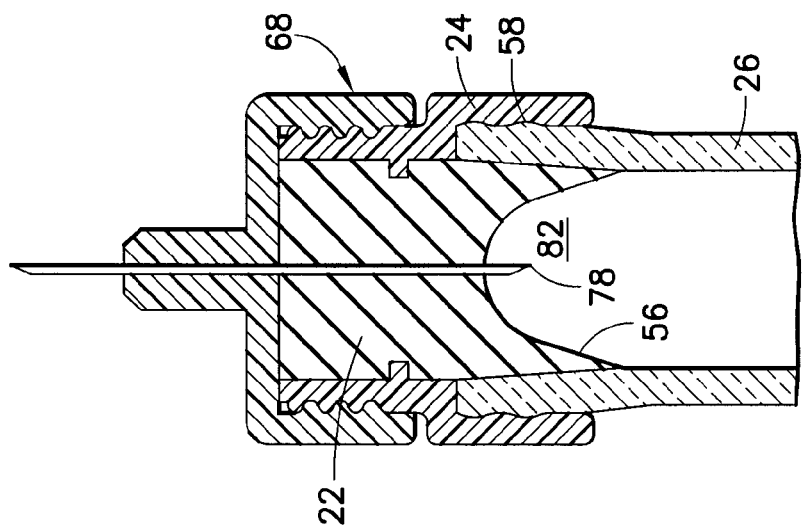
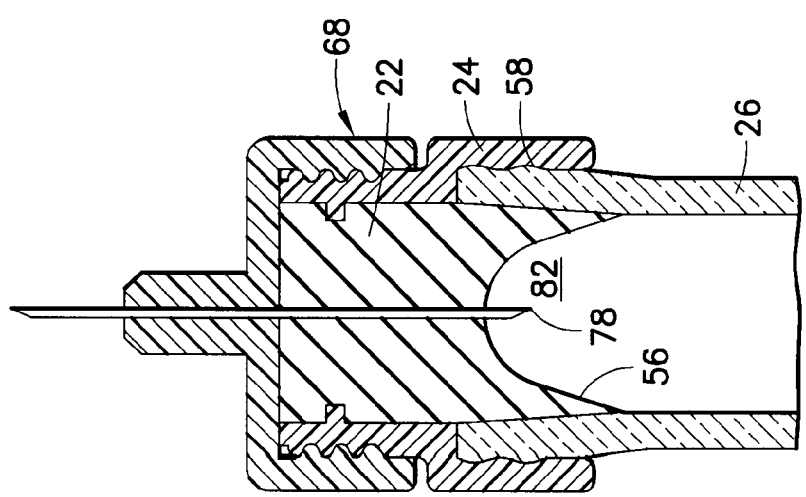

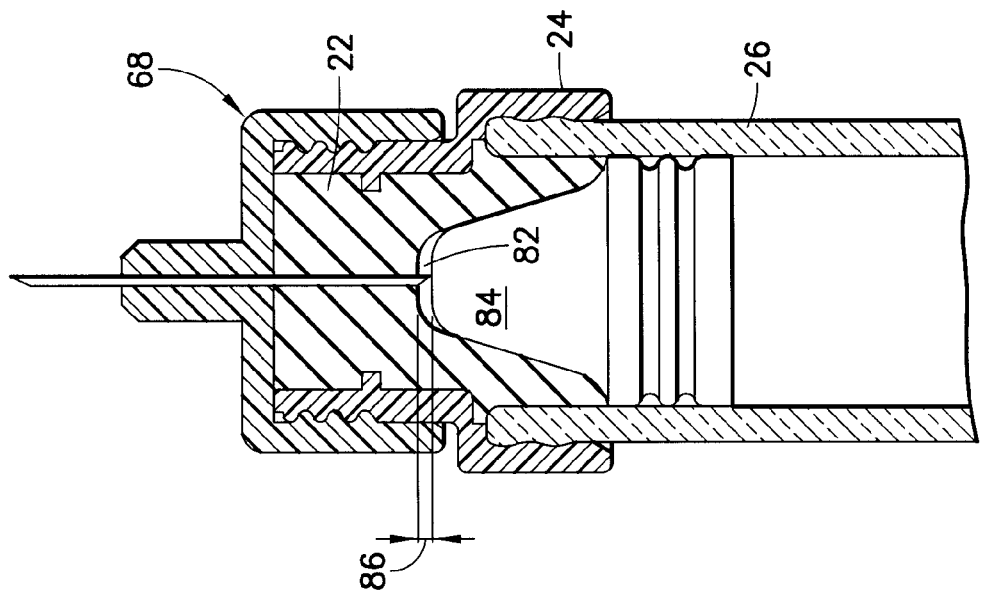
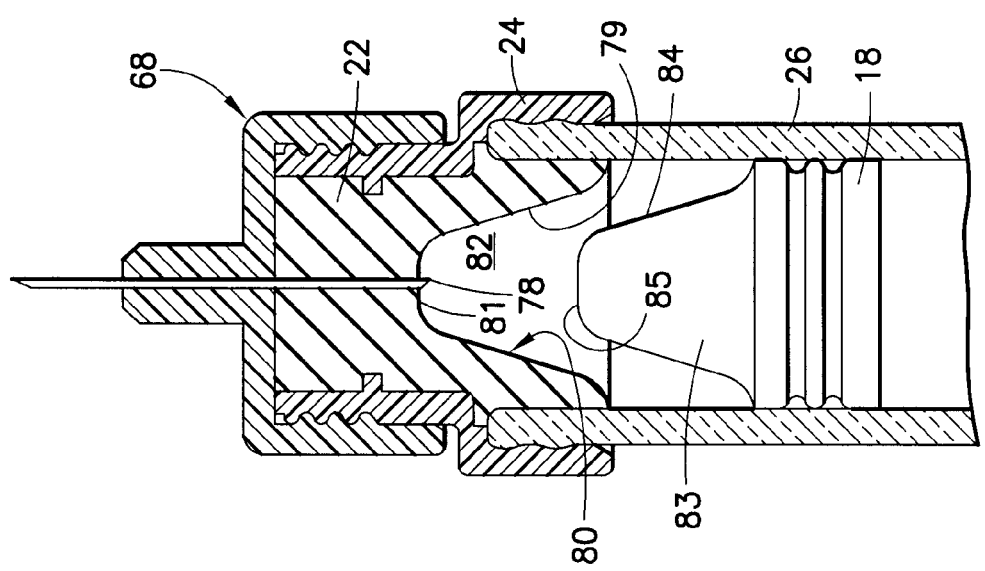

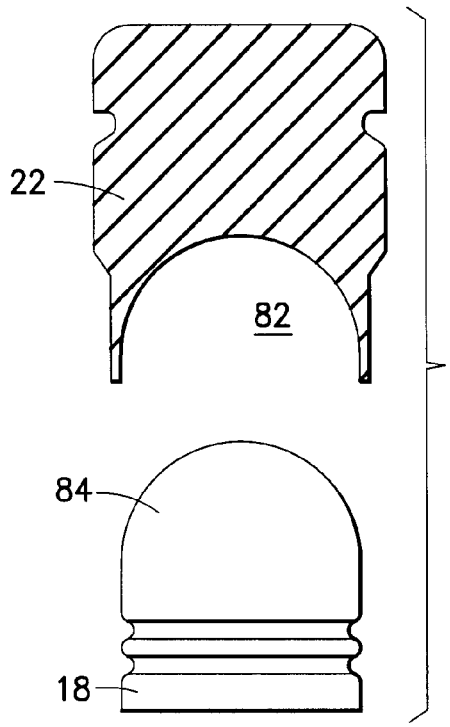 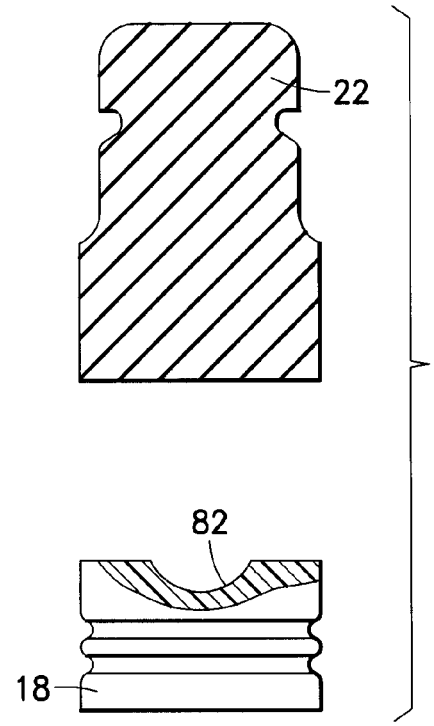
FIG.18    FIG.19
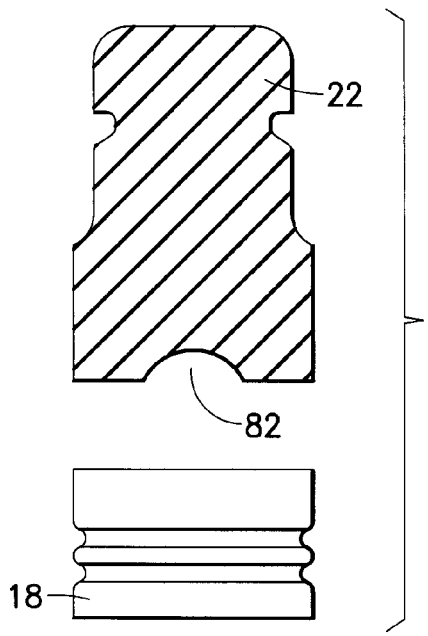 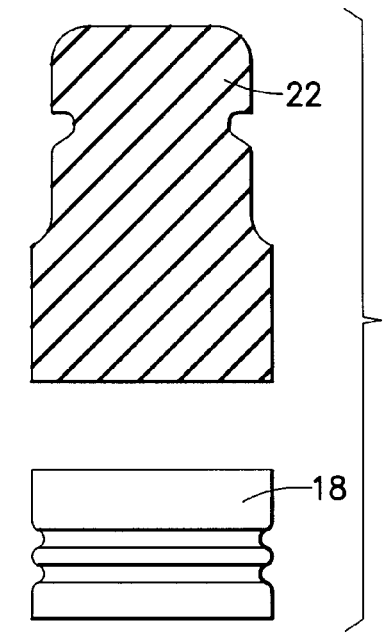
FIG.20    FIG.21

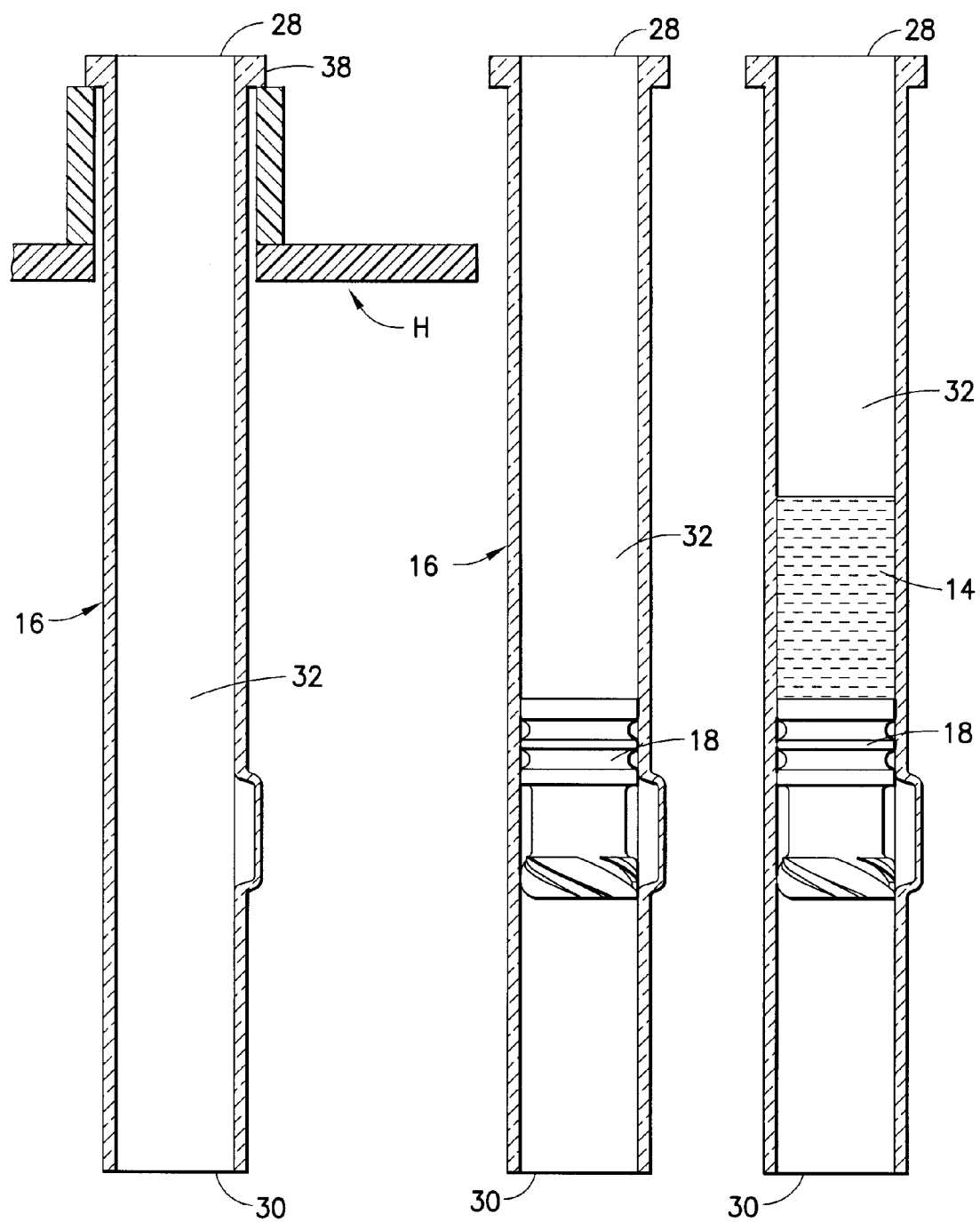

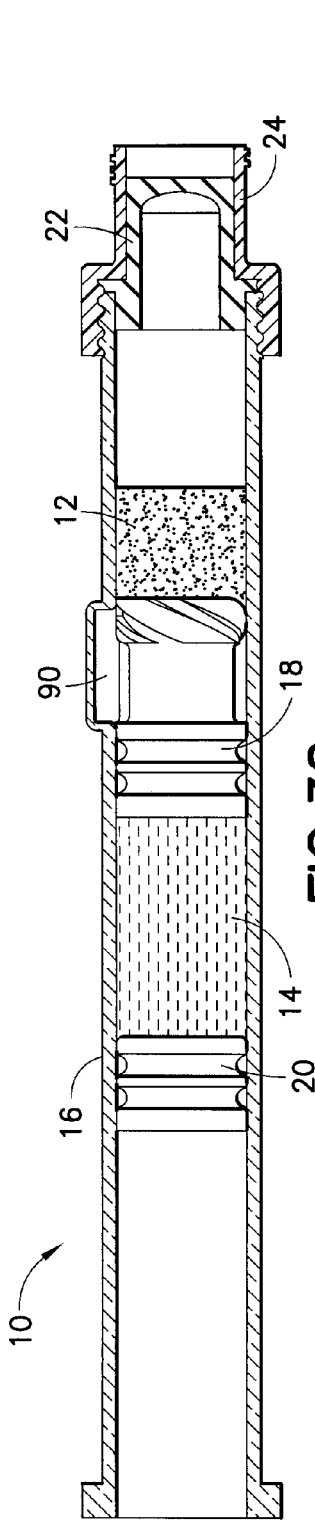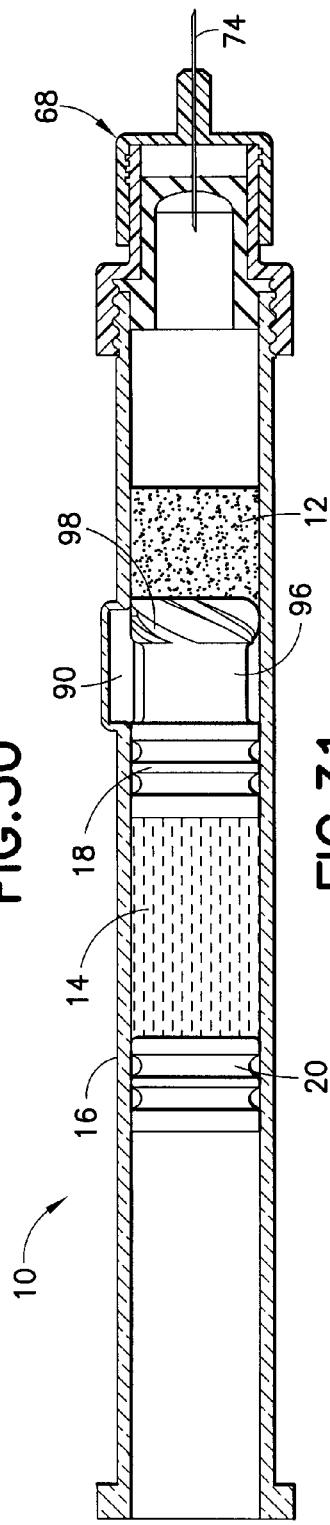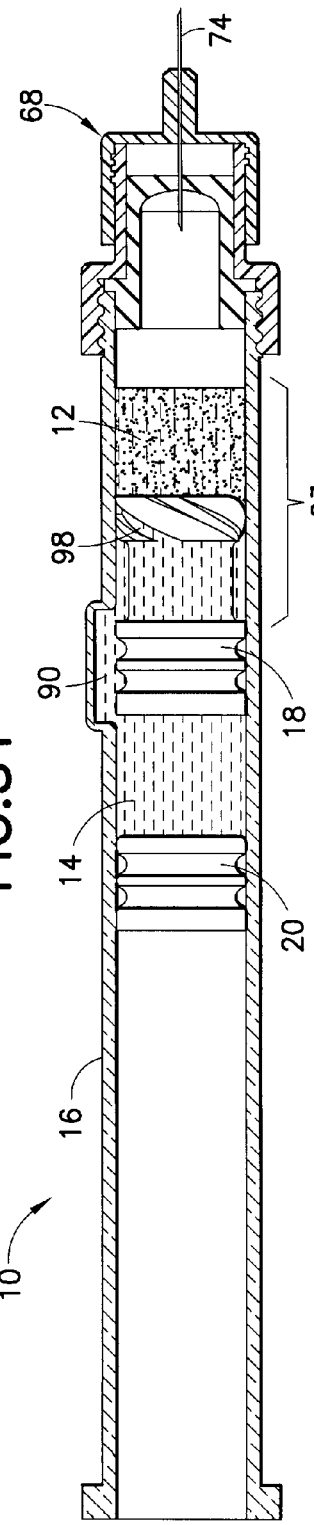

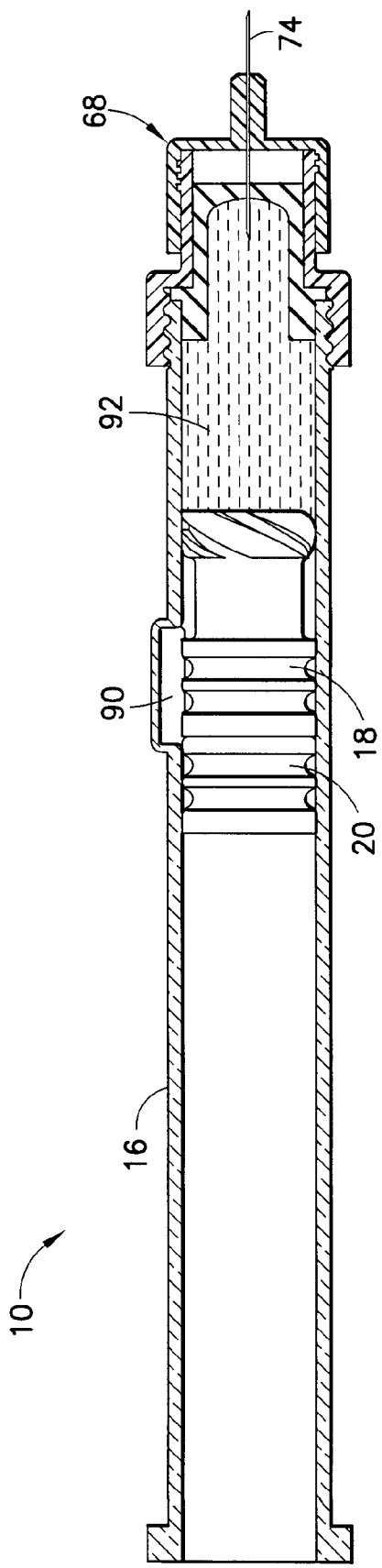
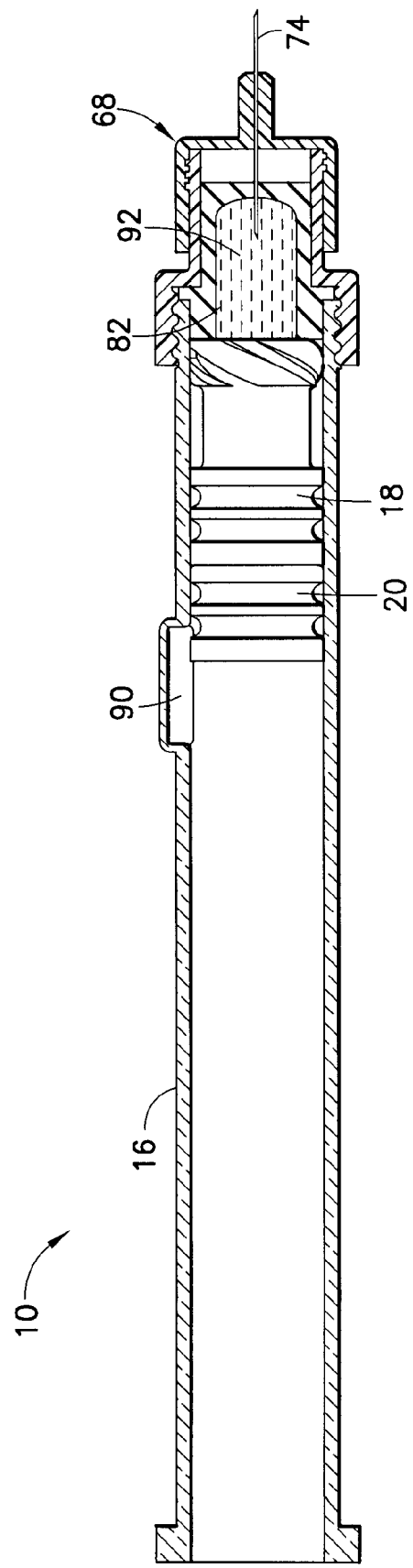

CARTRIDGE FOR POWDER AND LIQUID DRUG

CROSS-REFERENCE TO RELATED APPLICATIONS

This application claims priority to U.S. Provisional Patent Application No. 60/995,547, filed Sep. 27, 2007, and claims priority to U.S. Provisional Patent Application No. 61/011,255, filed Jan. 16, 2008, the entire contents of both of these applications being incorporated by reference herein.

BACKGROUND OF THE INVENTION

Reconstitution systems are known in the prior art. The systems typically include two components, a wet component and a dry component, which are mixed to form an injectable substance. The dry component is typically a lyophilized powder which contains one or more therapeutic agents. The wet component is a liquid diluent suitable for mixing with the dry component in forming a solution.

The dry component and the liquid component are maintained separately during storage. With a reconstitution cartridge or injector, the liquid and dry components are provided in the same cartridge or injection barrel with one or more seal elements being provided to separate the two components. Difficulties are encountered in the prior art in preparing such cartridges and injectors. In particular, the barrel of the cartridge or the injector is typically formed with a reduced-diameter distal, or patient, end configured to accommodate standard medical needle assemblies. The reduced-diameter distal end limits the ability to introduce the dry component in a dry state. There are limitations in the size of a stream of dry powder or the like being transmitted. The distal end of a typical cartridge or injector is too small to properly accept such a stream. The dry component is typically initially provided in a liquid form and introduced through the distal end of the barrel. The liquid is lyophilized in situ such that the dry component is produced in the device. The liquid form of the dry component is typically not introduced from the proximal end of the barrel since the liquid may leave residue along the barrel. This leads to not only potential loss of product but possible contamination issues.

SUMMARY OF THE INVENTION

A cartridge or injector for holding and mixing a medical product is provided herein including a tubular body having a cylindrical wall having first and second opposing ends. The wall includes inner and outer surfaces with the inner surface having a generally constant cross-section along at least a drug mixing area. A first stopper is slidably disposed within the wall between the first and second ends, the first stopper defining a liquid-tight seal with the inner surface. A second stopper is slidably disposed within the wall between the first stopper and the first end, the second stopper defining a liquid-tight seal with the inner surface. A flexible insert is disposed at or in proximity to the second end, the insert forming a liquid-tight seal with the wall, the insert being pierceable by a medical needle or other piercing instrument. A rigid retainer is fixed to the wall having an opening therein for providing access to the insert for piercing by a medical needle. The insert extends into the retainer and forms a liquid-tight seal across the opening. Advantageously, with the subject invention, a reconstitution assembly may be provided which has a sufficiently large distal opening during assembly which allows a dry component to be introduced into the device in a dry state.

These and other features of the invention will be better understood through a study of the following detailed description and accompanying drawings.

BRIEF DESCRIPTION OF THE DRAWINGS

FIGS. 5-6 are cross-sectional views of two different retainer configurations in accordance with the subject invention;

FIGS. 7-11 depict further configurations for retaining the flexible insert on the tubular body in accordance with the subject invention;

FIGS. 12-21 depict different configurations for defining the interface between a first stopper and flexible insert in accordance with the subject invention;

FIGS. 24-29 depict a filling process usable with the subject invention;

FIGS. 30-35 depict the subject invention in use; and,

DETAILED DESCRIPTION OF THE INVENTION

Figure 1:
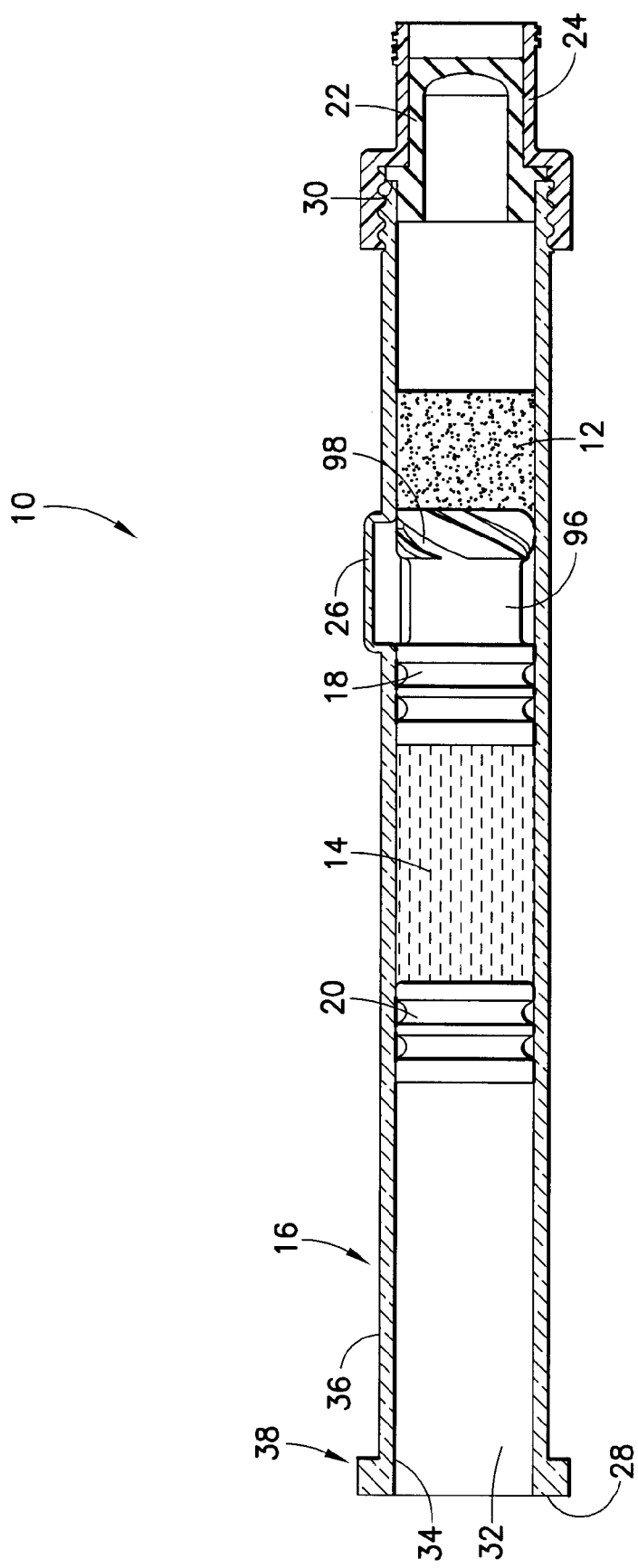
FIG. 1 is a plan view of a medical injector assembly formed in accordance with the subject invention.

With reference to FIG. 1, a medical injector assembly 10 is provided herein for causing reconstitution of a dry component 12 with a wet component 14 to form an injectable solution. The dry component 12 may be in the form of powder or granules, such as lyophilized powder or granules. The wet component 14 may be a liquid, syrup or slurry. The wet component 14 is selected to be compatible with the dry component 12 such that the wet component 14 acts as a diluent for the dry component 12. With mixing of the dry component 12 and the wet component 14, as described below, the two components 12, 14 together form a single solution of injectable product. It is to be understood that the dry component 12 may be mixed to be fully in solution with the wet component 14, or in partial solution, or not in solution with the dry component 12 being in suspension in the wet component 14. For purposes herein, all of these may be considered "reconstitution". One or more therapeutically active agents may be located in the dry component 12 and/or the wet component 14.

The assembly 10 generally includes a tubular body 16, a first stopper 18, a second stopper 20, a flexible insert 22, and a rigid retainer 24. The assembly 10 may be used as an injector, for example with a plunger being attached to the second stopper 20, or as a drug cartridge for use with an injector (e.g., a pen injector), as described below.

The tubular body 16 includes a cylindrical wall 26 with a first end 28 and a second end 30. The cylindrical wall 26 is preferably formed as a unitary piece and is preferably rigid. The cylindrical wall 26 may be formed of thermoplastic, glass, or combinations thereof. A lumen 32 is defined through the cylindrical wall 26. The cylindrical wall 26 also includes a inner surface 34 and an outer surface 36. Optionally, the tubular body 16 may include a flange 38 located to extend from the outer surface 36 at or near the first end 28.

The flexible insert 22 is located at or in proximity to the second end 30. The flexible insert 22 engages the wall 26 such that a liquid-tight seal is defined therebetween. Different configurations for defining the liquid-tight seal are described below.

The flexible insert 22 is formed of a material which is pierceable by a medical needle or other piercing instrument. Preferably, the flexible insert is formed of an elastomeric material, which may be a natural rubber, synthetic rubber or combinations thereof. Examples of suitable rubbers include butyl rubber and silicone rubber. Other flexible materials may be used which are consistent with the disclosure herein. Any material which is used should have good barrier properties and must be compatible with the dry and wet components 12, 14. It is also preferred that the flexible insert 22 be re-sealable such that upon removal of a medical needle which has pierced therethrough, any opening is re-sealed with sufficient integrity to prevent liquid flow therethrough. The assembly 10 may be used in conjunction with multiple doses, thus requiring a series of medical needles to pierce through the flexible insert 22. Re-sealing of the flexible insert 22 allows for such repeated dosing.

The rigid retainer 24 acts to hold the flexible insert 22 in place on the wall 26 and is formed of a rigid material, such as thermoplastic. Soft or elastomeric materials are avoided. The rigid retainer 24 is fixed to the wall 26 with the flexible insert 22 being encompassed by the rigid retainer 24. An opening 40 is provided through the rigid retainer 24 which provides access to the flexible insert 22. The opening 40 is configured to allow a medical needle to pass therethrough and to pierce the flexible insert 22. The flexible insert 22 extends into the rigid retainer 24 and defines a liquid-tight seal across the opening 40.

The flexible insert 22 and the rigid retainer 24 collectively define a liquid-tight seal at the second end 30 of the wall 26. Features 42 are defined on exterior portions of the rigid retainer 24 configured to receive in mounting engagement a medical needle assembly. In this manner, a medical needle assembly may be mounted onto the assembly 10. With the flexible insert 22 and the rigid retainer 24 providing a liquid-tight seal at the second end 30 and providing an arrangement for mountingly receiving a medical needle assembly, the second end 30 of the wall 26 need not be reduced in diameter as in the prior art. Rather, the second end 30 may be formed with a relatively large diameter, including being formed with a diameter the same or substantially the same as the first end 28. In this manner, the inner surface 34 may have a generally constant cross-section throughout at least a portion of the wall 26, including all or a substantial portion of the wall 26 (a substantial portion of the wall 26 may be taken as all of the wall 26 excepting out any end flared sections and any reconstitution features (such as reconstitution by-pass channels)). This arrangement permits the use of both the first and second ends 28, 30 in the filling of the assembly 10. In addition, the second end 30 may be formed with a sufficiently large diameter to permit the dry component 12 to be passed therethrough in a dry state in preparing the assembly 10, as described below.

With reference to FIG. 1, the dry and wet components 12, 14 may be disposed in the assembly 10 in conjunction with various arrangements which permit reconstitution. In a preferred arrangement, the dry component 12 is located to be between the first stopper 18 and the flexible insert 22. The wet component 14 is located to be between the first and second stoppers 18, 20. The first and second stoppers 18, 20 define liquid-tight seals with the inner surface 34 of the wall 26. As such, the wet component 14 is retained in the wall 26 and kept separate from the dry component 12. FIG. 1 depicts a storage, pre-use position where no medical needle is attached to the assembly 10 and the dry and wet components 12, 14 are kept separately.

The rigid retainer 24 preferably includes a first section 44 from which extends a barrel section 46. The barrel section 46 terminates at a free end 48. It is preferred that the opening 40 be formed through the free end 48. In addition, it is preferred that the features 42 for mountingly receiving a medical needle assembly be formed on the barrel section 46. It is further preferred that the first section 44 have a larger diameter than the barrel section 46. With the rigid retainer 24 fixed to the wall 26, it is preferred that the barrel section 46 extend outwardly distally beyond the second end 30 of the wall 26.

Figure 4:
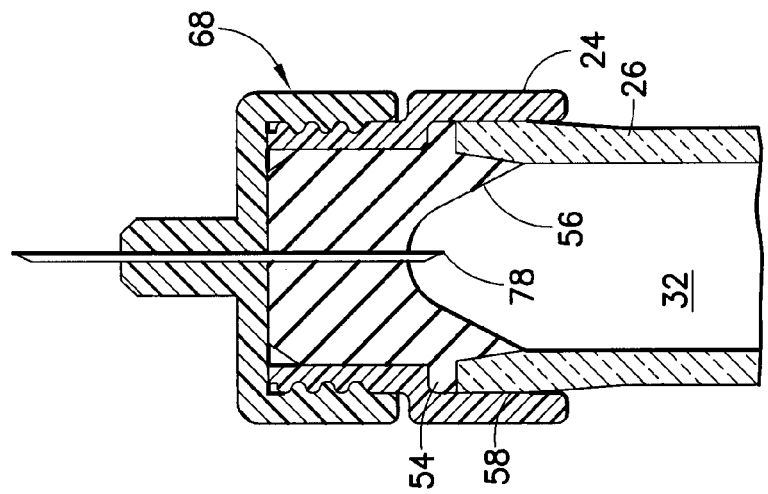
FIGS. 2-4 depict various configurations of retaining a flexible insert on a tubular body in accordance with the subject invention.
Figure 3:
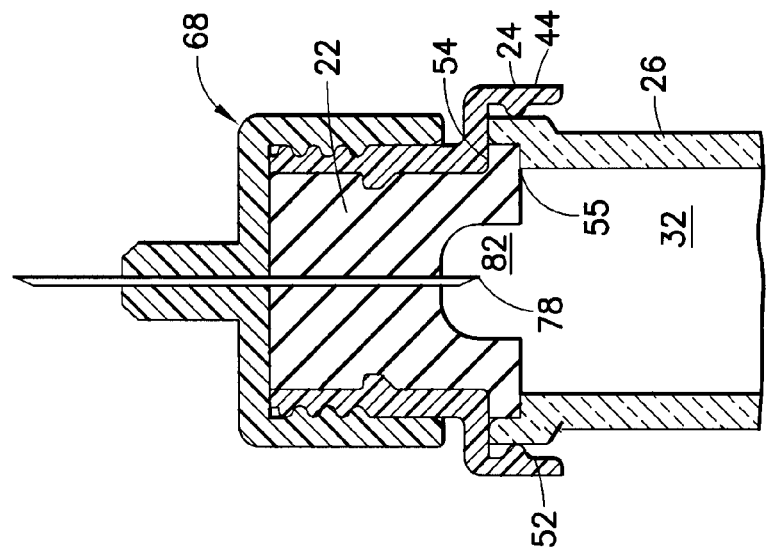
Figure 2:
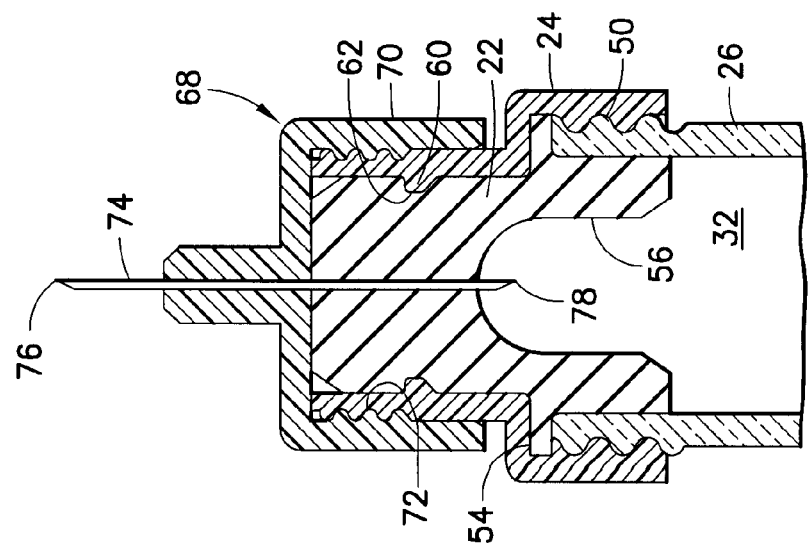
Figure 14:
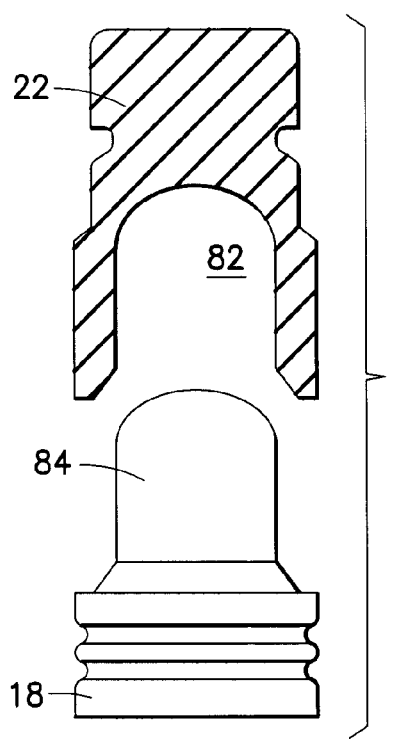
Figure 15:
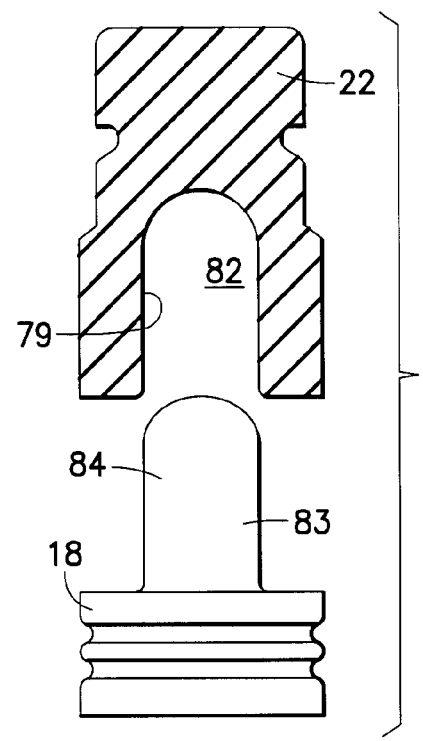
Figure 16:
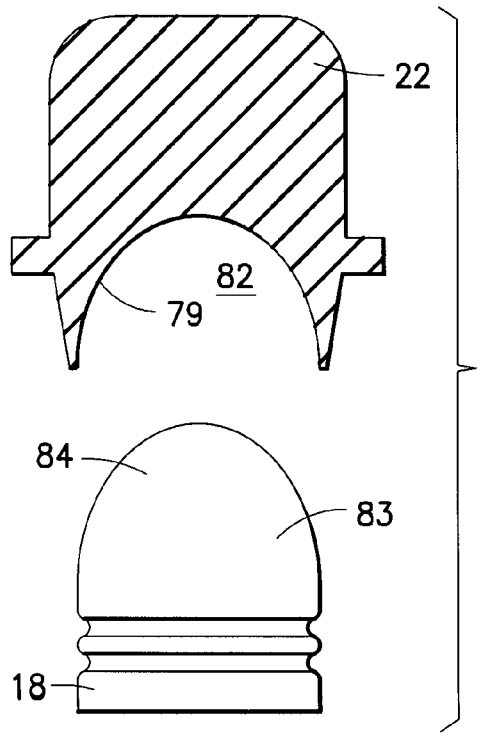
Figure 17:
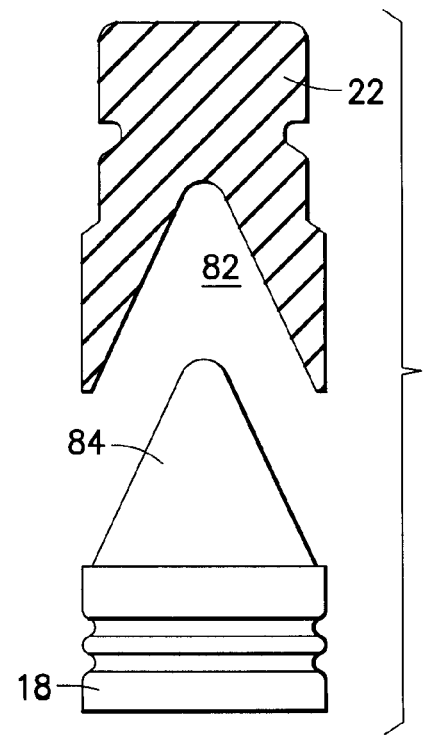

The rigid retainer 24 may be fixed to the wall 26 with any known configuration. With reference to FIGS. 2-4, the wall 26 and the first section 44 may be formed with cooperating threads 50. Other releasable mechanisms, such as a bayonet-type mechanism may be used. With reference to FIG. 3, the first section 44 may be configured to be fixed in a mechanical interference to the wall 26 (e.g. snap engagement or interference fit). To enhance the interengagement between the rigid retainer 24 and the wall 26, one or more detents 52 may be provided on the wall 26 and/or the first section 44 for enhancing the retaining force. The rigid retainer 24 may be permanently fixed to the wall 26 such as through mechanical interference, adhesive bonding, fusion and/or mechanical connection (e.g., crimping).

The flexible insert 22, as indicated above, defines a liquid-tight seal with the tubular body 16. In particular, the liquid-tight seal prevents any liquid from migrating from the lumen 32 and past the flexible insert 22. As shown in FIGS. 2-4, the flexible insert 22 may be provided with a shoulder 54 that is formed to extend between the rigid retainer 24 and portions of the wall 26. The shoulder 54 is shaped in size such that with the rigid retainer 24 being fixed to the wall 26, compressive forces are applied to the shoulder 54, thereby allowing for a liquid-tight seal to be defined between the shoulder 54 and the wall 26. A cut-out 55 may be defined in the second end 30 in which the shoulder 54 rests. To further enhance the sealing effect, the flexible insert 22 may include a sleeve portion 56 that extends into the lumen 32 in a proximal direction towards the first end 28. The sleeve portion 56 extends into the lumen 32 so as to overlap the second end 30. The sleeve portion 56 may be formed with a slightly larger diameter than the lumen 32 such that with insertion of the sleeve portion 56 into the lumen 32 a tight seal interface is defined against the inner surface 34.

The inner surface 34 may have a generally constant cross-section in proximity to the second end 30, as shown in FIG. 2. With the sleeve portion 56 being utilized, the wall 26 may have a flared section 58 adjacent to the second end 30 thus allowing for a larger cross-section of a inner surface 34 adjacent to the second end 30. In this manner, the sleeve portion 56 has less or no impact on reducing the diameter of the lumen 32. Thus, in comparing the configurations of FIGS. 2 and 4, the sleeve portion 56 in FIG. 4, allows for the lumen 32 to have a larger cross-section adjacent to the flexible insert 22, as compared to the arrangement in FIG. 2, due to the flared section 58. The interengagement between the rigid retainer 24 and the shoulder 54 also provides holding force for retaining the flexible insert 22. In addition, the flared section 58 may ease manufacturing by permitting easier insertion of the flexible insert 22 into the wall 26.

To enhance the ability of the rigid retainer 24 to hold the flexible insert 22, a locking rib 60 may be provided on the interior of the barrel section 46 formed to be nestingly received within a locking channel 62 formed in the flexible insert 22. As shown in FIG. 4, the locking rib 60 and the locking channel 62 are not necessary. Further, with reference to FIGS. 5 and 6, the location of the locking rib 60 and the locking channel 62 may be altered. Manufacturing concerns, such as shrinkage that may affect the features 42, may be taken into consideration in locating the locking rib 60. The interengagement of the locking rib 60 and the locking channel 62 minimizes axial removal of the flexible insert 22 relative to the rigid retainer 24.

With reference to FIG. 7, as a further mode of retaining the flexible insert 22, a step 64 may be formed on the flexible insert 22 shaped and sized to interferingly engage with engagement face 66 defined on the rigid retainer 24. Preferably, the engagement face 66 is defined by inwardly reducing the diameter of the barrel section 46 such that the engagement face 66 overlaps with the lumen 32.

Any combination of the shoulder 54, the locking rib 60/locking channel 62, and the step 64/engagement face 66, may be utilized in providing retention for the flexible insert 22. As shown in FIGS. 8-11, where the locking rib 60/locking channel 62 are used alone to retain the flexible insert 22, it is preferred that the sleeve portion 56 be provided with the flexible insert 22 to define a liquid-tight seal. The flared section 58 may be of different shapes, including being tapered, arcuate and irregular shapes, with the corresponding sleeve portion 56 being conformingly shaped to mate tightly with the flared section 58 to define a liquid-tight seal therewith.

The flexible insert 22 preferably extends into the barrel section 46 of the rigid retainer 24. In addition, the flexible insert 22 defines a liquid-tight seal across the opening 40. The liquid-tight seal may be defined by a tight interface between the flexible insert 22 and the rigid retainer 24, particularly at the interface with the barrel section 46. The flexible insert 22 may be slightly oversized to ensure a tight fit within the rigid retainer 24 in defining the liquid-tight seal.

With reference to FIGS. 2-4, a medical needle assembly 68 is shown mounted onto the rigid retainer 24. The medical needle assembly 68 includes a hub 70, having formed thereon features 72 for cooperating with the features 42 defined on the rigid retainer 24, and a needle cannula 74 fixed to the hub 70. Preferably, the features 42 and 72 are formed to allow for removable mounting of the medical needle assembly 68 such that the assembly 10 may be used with multiple injections. The barrel section 46 (FIG. 5) may be formed with a diameter which permits the hub 70 to be mounted thereto, with the hub 70 being dimensioned to a standard pen needle hub size, e.g., as specified in ISO 11608-2 Type A. The needle cannula 74 is provided with a sharpened distal end 76, formed for insertion into a patient, and a proximal end 78, which is also preferably sharpened. As shown in the figures, with the medical needle assembly 68 being mounted to the rigid retainer 24, the needle cannula 74 pierces through the flexible insert 22. The needle cannula 74 has sufficient length so that the proximal end 78 extends beyond the flexible insert 22 into communication with the lumen 32.

It is preferred that a proximal face 80 of the flexible insert 22 be provided with a distally extending recess 82 located to be defined about the needle cannula 74, with the needle cannula 74 extending through the flexible insert 22. As shown in FIGS. 2-4, the proximal end 78 of the needle cannula 74 is thus located within the recess 82. In addition, the recess 82, with the assembly 10 being in an inverted injection position, defines a gravitational low-point about the proximal end 78 during use. This provides an enhanced ability to utilize all liquid contained within the lumen 32 during an injection. As shown in the figures, the recess 82 may be defined to have a limited diameter, as particularly shown in FIGS. 2 and 3, or a tapered diameter extending generally from the width of the lumen 32, as shown in FIG. 4. Other configurations for the recess 82 are shown in FIGS. 7-18 and 20.

As described below, during use, the first stopper 18 will press against injectable solution located adjacent to the flexible insert 22 in urging injectable solution through the needle cannula 74. With the recess 82 being utilized, a protrusion 84 may be provided on the first stopper 18, particularly on a front end thereof, formed to extend into the recess 82 during use. With reference to FIGS. 12 and 13, the recess 82 and the protrusion 84 are shaped such that the recess 82 is complementarily sized and shaped to nestingly receive the protrusion 84. Preferably, the recess 82 and the protrusion 84 are provided with generally the same profile. The recess 82 and the protrusion 84 may be formed with different profiles (i.e., different three-dimensional shapes) so long the protrusion 84 is capable of forming a continuous seal thereabout when nestingly received in the recess 82. The seal acts to retain liquid in the recess 82.

It is noted that both the first stopper 18 and the flexible insert 22 are preferably formed from elastomeric material. To ensure tight engagement between the recess 82 and the protrusion 84, it is preferred that the protrusion 84 be dimensioned slightly larger than the recess 82 so that a liquid-tight seal is formed at the interface of the recess 82 and the protrusion 84 during use. With sliding advancement of the protrusion 84 into the recess 82, open volume is reduced with entrapped liquid having an ever increasing amount of pressure built up therein. A sufficiently tight seal between the recess 82 and the protrusion 84 is necessary to prevent the fluid from bypassing the protrusion 84 and migrating in a proximal direction towards the first end 28. It is also preferred that a gap 86 remain in the recess 82 with the protrusion 84 being fully extended therein. The proximal end 78 of the needle cannula 74 preferably extends into the gap 86. In this manner, the protrusion 84 does not seal off the proximal end 78 of the needle cannula 74 during use. It is further preferred that the proximal end 78 have a short extent into the recess 82. As such, a minimal amount of solution may collect about the needle cannula 74 gravitationally below the proximal end 78 during use.

As will be appreciated by those skilled in the art, various matched shaped configurations can be used for the recess 82 and the protrusion 84. The recess 82 may be formed with a sidewall 79 which terminates at a distal end 81, while the protrusion 84 may have a body 83 which terminates at a free end 85. The sidewall 79 and the body 83 may have generally circular or arcuate cross-sections along the respective lengths thereof, the diameters of the cross-sections being constant or varied to define an overall three-dimensional shape. For example, with reference to FIG. 15, the sidewall 79 and the body 83 may each generally have a right cylindrical shape—here, the cross-sectional shape being generally maintained constant. In contrast, with reference to FIG. 16, the sidewall 79 and the body 83 are tapered with the cross-sectional shape being varied. In addition, the protrusion 84 terminates at the free end 85. The free end 85 may be formed with various shapes, but is preferably rounded. Correspondingly, the distal end 81 of the recess 82 may be rounded about the needle cannula 74 including being complementarily formed to the free end 83. It is preferred that the recess 82 and the protrusion 84 be shaped such that initial contact is at radially outermost regions of the recess 82, with any further contact being directed radially-inwardly. As such, a pocket is initially defined between the recess 82 and the protrusion 84 which is sealingly cut-off from the lumen 32 with the pocket decreasing as the protrusion 84 is further inserted into the recess 82. As shown in FIGS. 12-18, generally cylindrical, arcuate, hemi-spherical, and conical shapes may be used to define the recess 82 and the protrusion 84, as well as other regular and irregular three-dimensional shapes.

With reference to FIG. 19, although not preferred, the recess 82 may be formed on the first stopper 18. This would allow for a pocket of liquid to collect within the recess 82 during use and about the proximal end 78 of the needle cannula 74. As shown in FIGS. 20 and 21, the recess 82 can be used without the protrusion 84 (FIG. 20) and the recess 82 and the protrusion 84 can both also be avoided (FIG. 21). Where the protrusion 84 is not used, it is preferred that the first stopper 18 be formed to shape-matingly engage at least a portion of the proximal face 80 of the flexible insert 22. Thus, as shown in FIG. 20, the first stopper 18 may be formed to engage in face-to-face engagement with the proximal face 80 about the recess 82, whereas, as shown in FIG. 21, the first stopper 18 may be formed to engage in full face-to-face contact with the proximal face 80.

Figure 22:
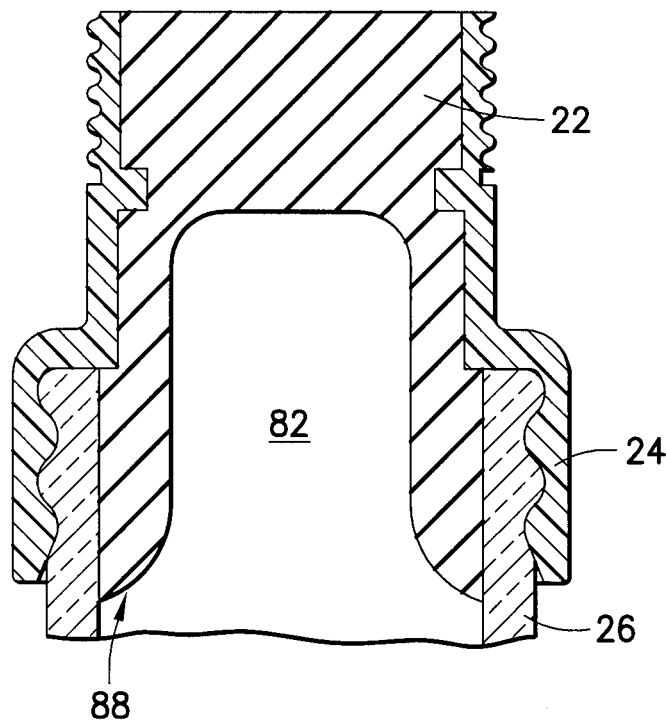
FIG. 22 depicts a rounded corner formed on the flexible insert in accordance with the subject invention.

As a further enhancement to the flexible insert 22, and with reference to FIG. 22, it is preferred that the proximalmost portion 88 of the flexible insert 22 be formed with an inwardly-directed rounded edge directed towards the center of the lumen 32. In this manner, liquid urged against the proximal face 80 shall be directed towards the center of the lumen 32 and away from the wall 26. The proximalmost portion 88 may be defined on the sleeve portion 56, as shown in FIG. 22. Likewise, the proximalmost portion 88 may be defined at the rim of the recess 82, without the sleeve portion 56, as shown in FIG. 3. Although not shown in FIG. 3, preferably, the proximalmost portion 88 is rounded.

Figure 23:
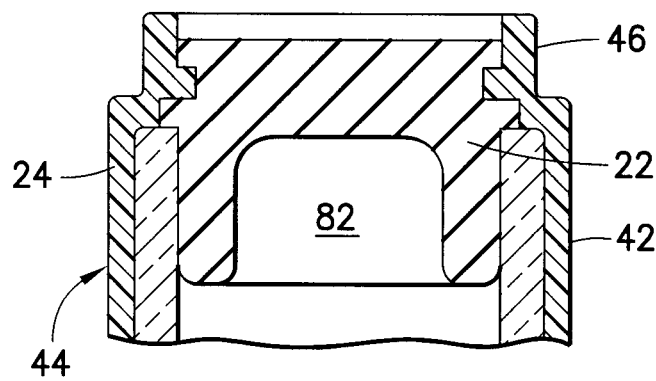
FIG. 23 depicts an alternative configuration of the flexible insert in the retainer in accordance with the subject invention.
Figure 27:
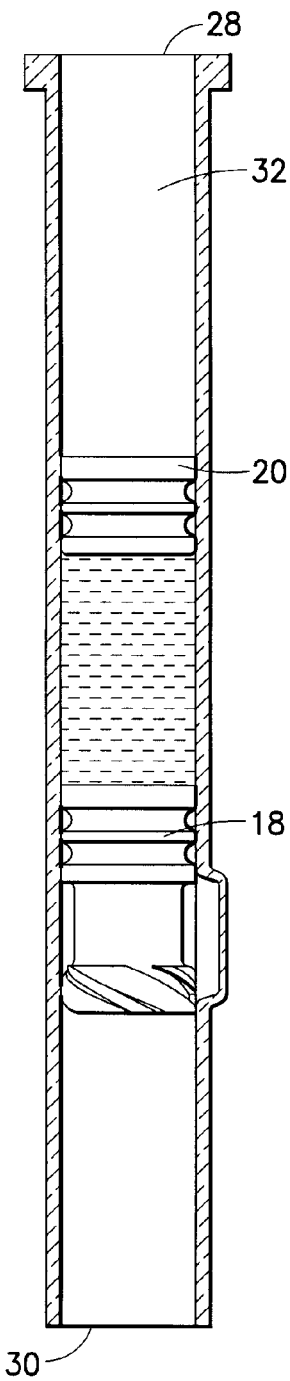

With reference to FIG. 23, the rigid retainer 24 may be defined to have the features 42 defined on the first section 44. With this arrangement, the medical needle assembly 68 may be mounted onto the rigid retainer 24 so as to encompass a portion of the wall 26. The barrel section 46 may thus be formed with a shorter length.

Figure 28:
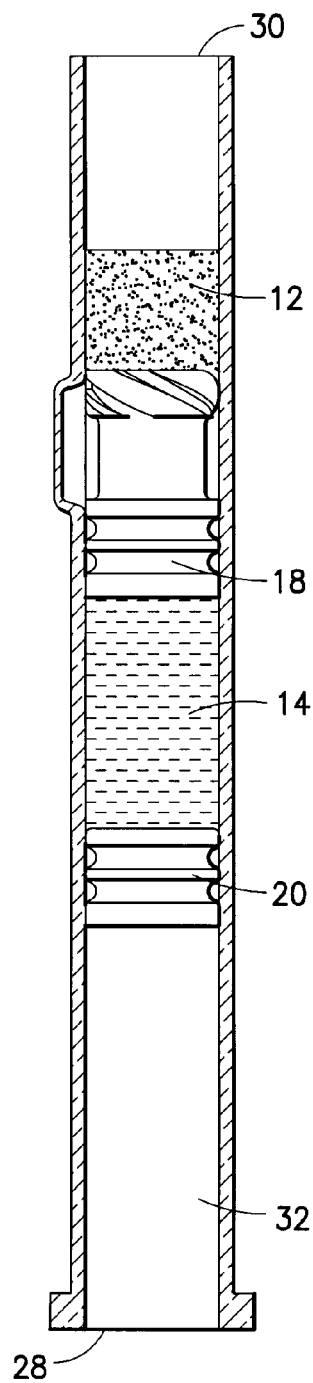
Figure 29:
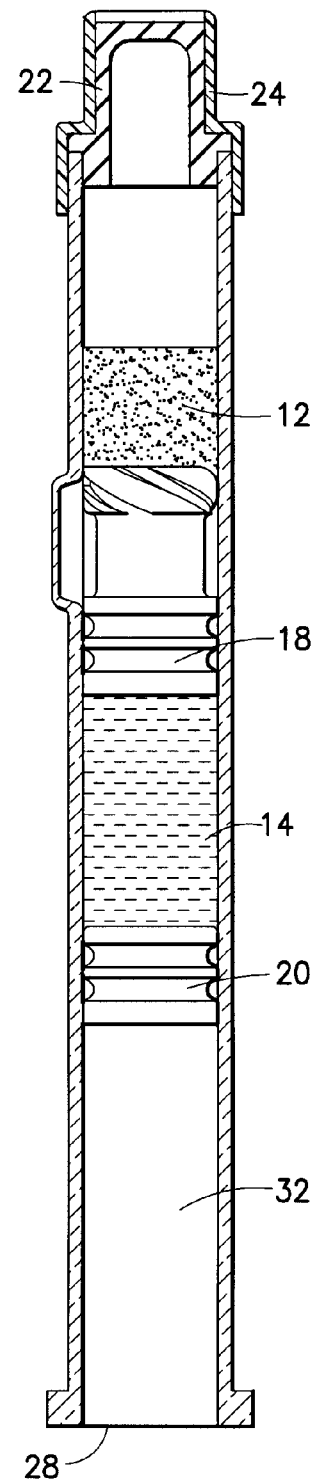

FIGS. 24-29 illustrate a method by which the assembly 10 may be prepared. With reference to FIG. 24, the tubular body 16 is placed into an upright position with the first end 28 extending upwardly. If the flange 38 is provided, the flange 38 may be placed onto a holder H to maintain the tubular body 16 in a fixed position. Next, with reference to FIG. 25, the first stopper 18 is placed within the wall 26 between the first and second ends 28, 30. Thereafter, and as shown in FIG. 26, the wet component 14 is deposited through the first end 28 and on top of the first stopper 18. The second stopper 20 is inserted into the tubular body 16 through the first end 28 so as to define a seal for the wet component 14. A vent tube may be used to allow for proper placement of the second stopper 20. To allow for filling equipment to be located only from one side of the assembly 10, the tubular body 16 is flipped so that the second end 30 is facing upwardly, as shown in FIG. 28. Thereafter, the dry component 12 is deposited, in a dry state, into the wall 26 atop the first stopper 18. The flexible insert 22 is placed onto the wall 26 and the rigid retainer 24 is caused to be fixed to the wall 26, thereby providing a seal for the dry component 12. The subject invention allows for a sufficiently large opening to be formed in the wall 26 to permit dry filling, while through the rigid retainer 24, allows for use of a pen needle assembly having a hub smaller in diameter than the opening in the wall 26. Thus, a standard pen needle assembly may be used where there is dry filling.

As will be appreciated by those skilled in the art, the assembly 10 may be filled through only the first end 28. Here, the flexible insert 22 is first fixed to the wall 26 with the rigid retainer 24. Thereafter, the dry component 12, the first stopper 18, the wet component 14, and the second stopper 20 are loaded into the tubular body 16 in sequence. A vent tube may be used to permit venting as necessary. This method can be used where concerns over the dry component 12 causing contamination along the tubular body 16 is minimal.

The tubular body 16, the first stopper 18 and the second stopper 20 may be configured in any known arrangement to permit reconstitution of the dry and wet components 12, 14. By way of non-limiting example, and with reference to FIGS. 30-34, at least one bypass channel 90, as is known in the prior art, may be defined in the tubular body 16 to facilitate reconstitution. With the bypass channel 90, and as shown in FIGS. 30-32, the first and second stoppers 18, 20 are initially located proximally of the bypass channel 90. As pressure is applied to the second stopper 20, the first stopper 18 is displaced under force transmitted by the wet component 14. Pressure continues to be applied to the second stopper 20, and with sufficient displacement of the first stopper 18, the first stopper 18 comes into alignment with the bypass channel 90. Thereafter, with further advancement of the second stopper 20, the wet component 14 is forced by the second stopper 20 through the bypass channel 90, past the first stopper 18, and into engagement with the dry component 12. The dry and wet components 12, 14 mix to form an injectable solution or suspension 92. The pressure may be applied to the second stopper 20 by a plunger which is manually driven, such as with a standard syringe, or driven by an injector, such as a pen injector. With reference to FIG. 33, with sufficient displacement of the second stopper 20, the second stopper 20 comes into direct engagement with the first stopper 18. Further advancement causes the first and second stoppers 18, 20 to seal the by-pass channel 90 from the injectable solution or suspension 92. The assembly 10 is then ready for injection.

The area of the wall 26 where the mixing occurs corresponds to a drug mixing area 93. Through the area 93, it is preferred that the inner surface 34 have a constant cross-section.

Depending on the configuration of the tubular body 16, the medical needle assembly 68 may need to be mounted to the rigid retainer 24 prior to the reconstitution. As such, the needle cannula 74 may act as a vent during the reconstitution process to allow for any gases trapped within the lumen 32 to be expelled. Thus, as shown in FIG. 31, the medical needle assembly 68 is mounted prior to advancement of the second stopper 20.

In addition, other modes of permitting reconstitution are usable with the assembly 10. For example, the first stopper 18 may be provided with a valve which permits the wet component 14 to pass therethrough. With these other arrangements, the bypass channel 90 need not be provided.

Figure 35:
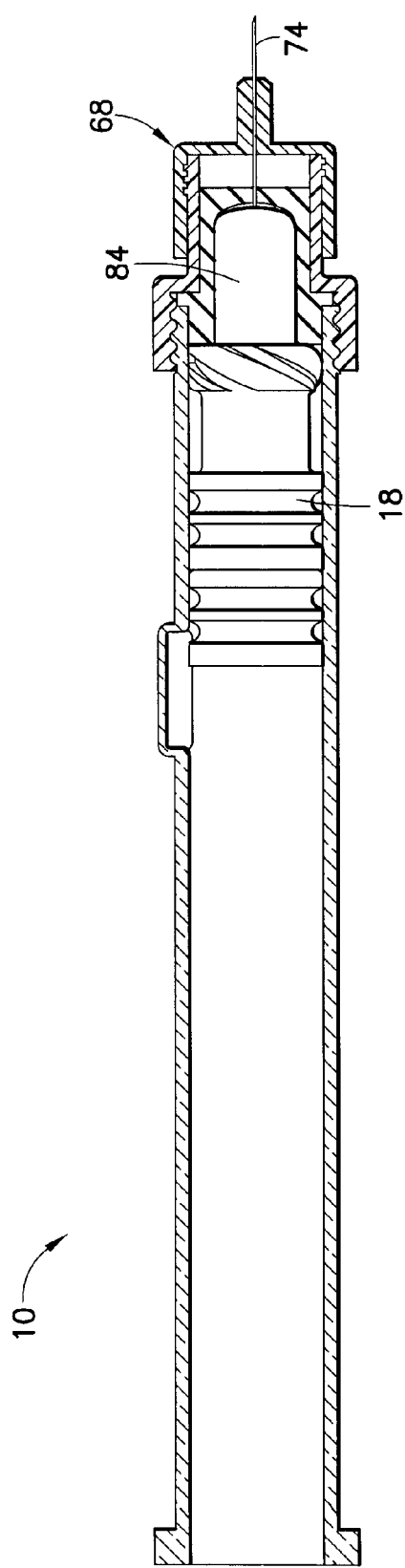

With the assembly 10 being ready for injection as shown in FIG. 33, the assembly 10 may be used to inject the injectable solution or suspension 92 in one or more doses. Each dose should be accompanied with a change of the medical needle assembly 68. Depending on the amount of dosing, as shown in FIG. 34, the first stopper 18 may come into contact with the flexible insert 22 and "bottom out". Further dosing will not be achievable. Thus, any of the injectable solution or suspension 92 trapped in the recess 82 will go unused. With reference to FIG. 35, if the protrusion 84 is utilized, a more efficient and complete usage of the injectable solution or suspension 92 may be achieved.

Any configuration for the first and second stoppers 18, 20 may be utilized which allows for the first and second stoppers 18, 20 to slide within the wall 26 and to define a liquid-tight seal therewith. As shown in the figures, the first and second stoppers 18, 20 may be provided with one or more sealing ribs 94, as is well known in the art. In addition, a film or oil may be provided on the inner surface 34 to enhance the sealing and/or sliding ability of the first and second stoppers 18, 20. The first and second stoppers 18, 20 may be formed of the same material as the flexible insert 22.

Further, the first stopper 18 may be provided with a secondary portion 96 having mixing channels 98 defined therein. The secondary portion 96 and the mixing channels 98 may be formed in accordance with U.S. Pat. Nos. 4,613,326 and/or 5,489,266, the entire contents of which are hereby incorporated by reference. The mixing channels 98 allow for a vortex to be formed in the wet component 14 during reconstitution, thereby enhancing the mixing effect of the wet component 14 with the dry component 12. In particular, the wet component 14 passes through the mixing channels 98 after by-passing the first stopper 18. The mixing channels 98 are helically or transversely disposed on the circumference of the secondary portion 96, thus, imparting a radial direction to the flow of the wet component 14. This radial direction causes the wet'component 14 to spin into contact with the dry component 12 resulting in a more agitated mixing.

Figure 36:
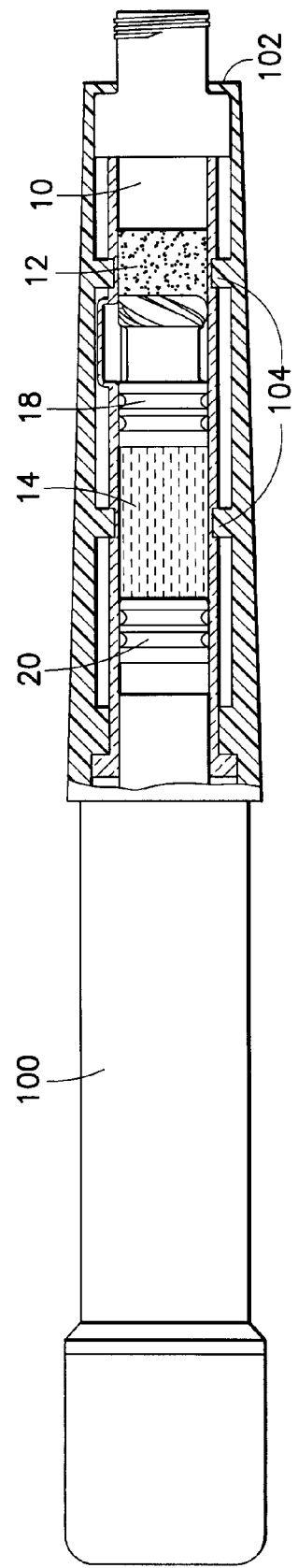
FIG. 36 depicts the medical injector assembly of the subject invention in use as a cartridge.

With reference to FIG. 36, the assembly 10 is shown as a cartridge in a pen injector 100. The outer surface 36 may be formed with features 104 for cooperating with the pen injector 100 to fixedly or releasably retain the assembly 10 within the pen injector 100. Replacement of the assembly 10 shall depend on whether the pen injector 100 is intended to be a single use or a multiple-use device. Further, as shown in FIG. 36, it is preferred that the pen injector 100 have an open distal end 102 through which the rigid retainer 24 may extend. Preferably, the features 42 formed on the assembly 10 are exposed to permit mounting thereon of the medical needle assembly 68. The pen injector 100 may be used to adjust dose volume during administration of the injectable solution or suspension 92 after reconstitution.

What is claimed is:

1. A cartridge for holding and mixing a medical product comprising:
    a tubular body having a cylindrical wall with first and second opposing ends, said wall having inner and outer surfaces, said inner surface having a generally constant cross-section extending from said second end and along at least a drug mixing area;
    a first stopper slidably disposed within said wall between said first and second ends, said first stopper defining a liquid-tight seal with said inner surface and having a front end;
    a second stopper slidably disposed within said wall between said first stopper and said first end, said second stopper defining a liquid-tight seal with said inner surface;
    a flexible insert disposed at or in proximity to said second end, said insert forming a liquid-tight seal with said wall, said insert having a recess formed therein being complementarily sized and shaped to at least partially nestingly receive said front end of said first stopper; and,
    a retainer fixed to said outer surface of said wall at said second end, said retainer having an opening therein for providing access to said insert for piercing by a medical needle, wherein, said insert extends into said retainer and forms a liquid-tight seal across said opening.

2. A cartridge as in claim 1, wherein said retainer is fixed to said second end of said tubular body via mechanical interference between said retainer and said tubular body.

3. A cartridge as in claim 1, wherein said tubular body is formed from a material selected from the group consisting of thermoplastic and glass.

4. A cartridge as in claim 1, wherein said front end of said first stopper includes a body which terminates at a free end.

5. A cartridge as in claim 4, wherein said body is formed with an arcuate cross-section along the length thereof.

6. A cartridge as in claim 5, wherein said arcuate cross-section is constant.

7. A cartridge as in claim 5, wherein said arcuate cross-section is not constant.

8. A cartridge as in claim 4, wherein said free end is rounded.

9. A cartridge as in claim 1, wherein said inner surface has defined therein a bypass channel.

10. A cartridge as in claim 9, wherein the medical product includes a wet component disposed between said first and second stoppers, and a dry component disposed between said first stopper and said second end, wherein movement of said second stopper towards said second end will cause compression of the wet component, said movement of said second stopper causing said wet component to pass through said bypass channel and to mix with said dry component.

11. A cartridge as in claim 10, wherein said first stopper includes mixing means for enhancing mixing of said wet component and said dry component.

12. A cartridge as in claim 11, wherein said mixing means comprises mixing channels defined in said first stopper.

13. A cartridge as in claim 1, wherein the medical product includes a wet component disposed between said first and second stoppers, and a dry component disposed between said first stopper and said second end, wherein movement of said second stopper towards said second end will cause compression of the wet component.

14. A cartridge as in claim 1, wherein said inner surface has a generally constant cross-section along a substantial portion of said wall.

15. An article for holding and mixing a medical product comprising:
    a tubular body having a cylindrical wall with first and second opposing ends, said wall having inner and outer surfaces, said inner surface having a generally constant cross-section extending from said second end and along a substantial portion of said wall;
    a first stopper slidably disposed within said wall between said first and second ends, said first stopper defining a liquid-tight seal with said inner surface;
    a second stopper slidably disposed within said wall between said first stopper and said first end, said second stopper defining a liquid-tight seal with said inner surface;
    a flexible insert at least partially disposed inside said inner surface at or in proximity to said second end, said insert forming a liquid-tight seal with said wall; and,
    a rigid retainer having a first portion fixed to said outer surface of said wall at said second end and a barrel-shaped portion with an outer surface formed to cooperatively engage a hub of a medical needle assembly, said first portion having a larger diameter than said barrel-shaped portion, said barrel-shaped portion extending outwardly from said wall and terminating at a free end with an opening therein for providing access to said insert for piercing by a medical needle, wherein, said insert extends from said tubular body and into said barrel-shaped portion and forms a liquid-tight seal across said opening.

16. An article as in claim 15, wherein the article is a cartridge.

17. An article as in claim 15, wherein the article is an injector.

* * * * *

UNITED STATES PATENT AND TRADEMARK OFFICE
CERTIFICATE OF CORRECTION

PATENT NO. : 8,469,923 B2
APPLICATION NO. : 12/679508
DATED : June 25, 2013
INVENTOR(S) : Vedrine et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 479 days.

Signed and Sealed this
Eighth Day of September, 2015

Michelle K. Lee
*Director of the United States Patent and Trademark Office*